United States Patent

Öhman et al.

[11] Patent Number: 5,995,209
[45] Date of Patent: Nov. 30, 1999

[54] APPARATUS FOR CONTINUOUSLY MEASURING PHYSICAL AND CHEMICAL PARAMETERS IN A FLUID FLOW

[75] Inventors: Ove Öhman; Björn Ekström; Peter Norlin, all of Uppsala, Sweden

[73] Assignee: Pharmacia Biotech AB, Uppsala, Sweden

[21] Appl. No.: 08/945,337
[22] PCT Filed: Apr. 25, 1996
[86] PCT No.: PCT/SE96/00548
§ 371 Date: Oct. 27, 1997
§ 102(e) Date: Oct. 27, 1997
[87] PCT Pub. No.: WO96/34282
PCT Pub. Date: Oct. 31, 1996

[30] Foreign Application Priority Data

Apr. 27, 1995 [SE] Sweden ................................. 9501592

[51] Int. Cl.⁶ .................................................. G01N 21/00
[52] U.S. Cl. ........................ 356/72; 356/73; 356/246
[58] Field of Search ........................... 356/72, 73, 246

[56] References Cited

U.S. PATENT DOCUMENTS

| | | | |
|---|---|---|---|
| 4,462,962 | 7/1984 | Baba et al. | 356/72 |
| 4,555,936 | 12/1985 | Scott | 356/436 |
| 4,883,354 | 11/1989 | Sun et al. | 356/72 |
| 5,408,313 | 4/1995 | Ponstingl et al. | |
| 5,446,531 | 8/1995 | Boyer et al. | 356/72 |

FOREIGN PATENT DOCUMENTS

0333939 A2  9/1989  European Pat. Off. .

*Primary Examiner*—Robert H. Kim
*Attorney, Agent, or Firm*—Birch, Stewart, Kolasch & Birch, LLP

[57] ABSTRACT

The present invention is drawn to an apparatus for continuously measuring physical and chemical parameters in a fluid cell comprising a single flow cell having a fluid interface for conducting the fluid through the flow cell, an electrical interface connected to at least one first means provided in the flow cell wall for measuring at least one first parameter of the fluid in the flow cell, and an optical interface for transmitting light into the flow cell and for receiving light from the flow cell to measure at least one second parameter of the fluid in the flow cell.

1 Claim, 1 Drawing Sheet

APPARATUS FOR CONTINUOUSLY MEASURING PHYSICAL AND CHEMICAL PARAMETERS IN A FLUID FLOW

TECHNICAL FIELD

The invention relates to an apparatus for continuously measuring physical and chemical parameters in a fluid flow.

BACKGROUND OF THE INVENTION

Liquid chromatography is a widely used technique for separation and analysis of chemical compounds. The basic principle of the chromatography technique is to let a test sample travel through a column containing a supporting medium, and there interact with substances of two different phases, namely a mobile phase and a stationary phase. Different sample components will interact to different degrees with the two phases, and those interacting more strongly with the stationary phase will eventually be lagging those preferring the mobile phase. The result is a separation of the test sample components during the passage of the column.

To detect the sample components as they leave the separation column, several detector techniques are employed.

So far, separate detectors have been used to detect different parameters of the sample components as they leave the separation column. If more when one parameter are to be measured, different detectors would have to be interconnected by means of e.g. a flexible tubing in order to carry out the measurement.

BRIEF DESCRIPTION OF THE INVENTION

The object of the invention is to bring about an apparatus which makes it possible to measure more than one parameter in one and the same volume of a fluid flow.

This is attained by the apparatus according to the invention in that it comprises a single flow cell having a fluid interface for conducting the fluid through the flow cell, an electrical interface connected to at least one first means provided in the flow cell wall for measuring at least one first parameter of the fluid in the flow cell, and an optical interface for transmitting light into the flow cell and for receiving light from the flow cell to measure at least one second parameter of the fluid in the flow cell.

BRIEF DESCRIPTION OF THE DRAWING

The invention will be described more in detail below with reference to the appended drawing, on which

PREFERRED EMBODIMENTS OF THE INVENTION

Figure 1:
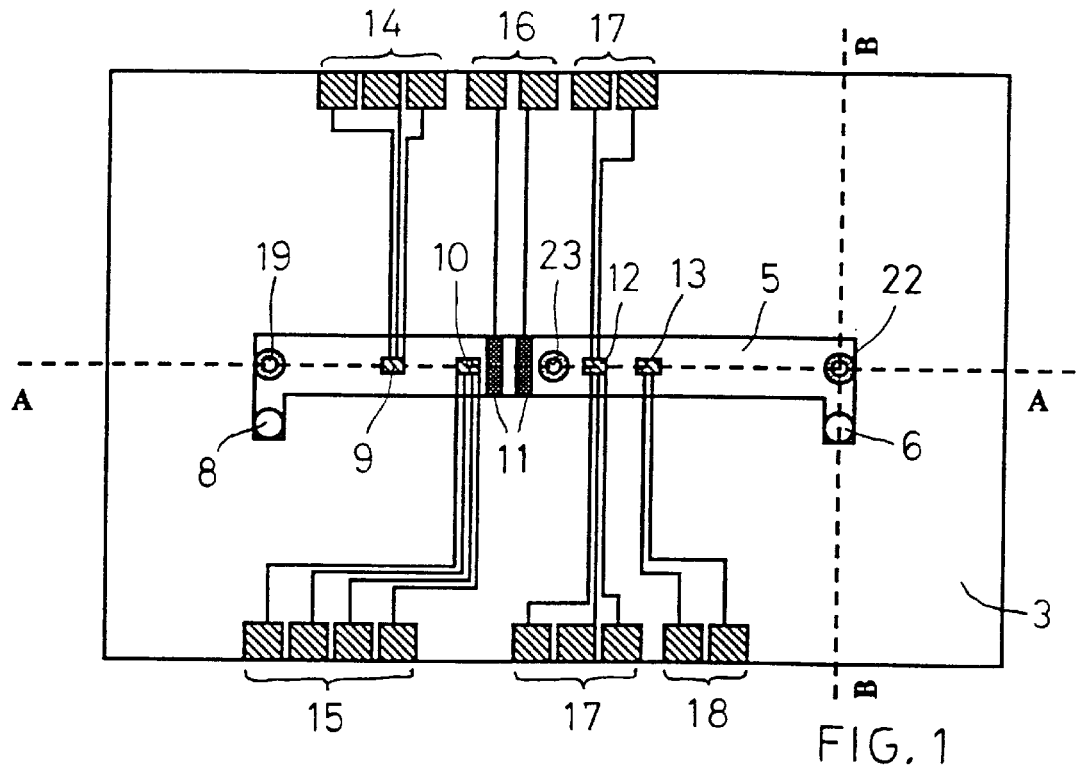
FIG. 1 is a plan view of an embodiment of a sensor chip for a flow cell according to the invention.
Figure 2:
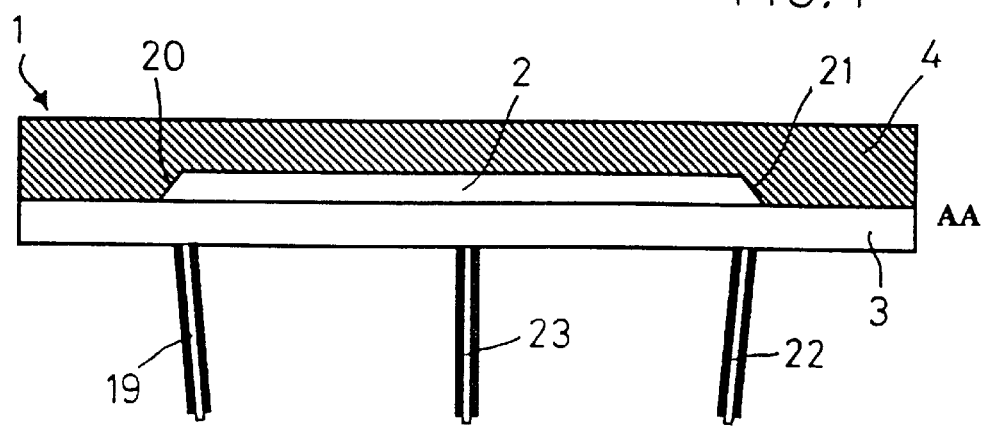
FIG. 2 is a schematic longitudinal sectional view of an embodiment of a flow cell according to the invention along line A—A as indicated on the sensor chip in FIG. 1.

FIG. 2 is a schematic longitudinal sectional view of an embodiment of a flow cell 1 according to the invention along line A—A as indicated in FIG. 1.

In the flow cell 1, a flow channel 2 is defined between a sensor chip 3, a plan view of which is shown in FIG. 1, and a silicon wafer 4, which has been anisotropically etched with a KOH solution to produce the flow channel 2. As is well known per se, this etching process will produce a flow channel with sloped or inclined side-walls as apparent from FIGS. 2 and 3 if mask/substrate orientation and etchant are choosen correctly.

It is to be understood that the wafer 4 does not necessarily have to be a silicon wafer but that other materials are possible.

In the embodiment shown, the sensor chip 3 is transparent and made of quartz. However, the sensor chip 3 does not have to be made of quartz but other materials are also possible.

On the sensor chip 3 in FIG. 1, the bottom area of the flow channel 2 is denoted 5. That bottom area 5 of the flow channel 2 can also be termed the measurement area of the flow cell 1.

Figure 3:
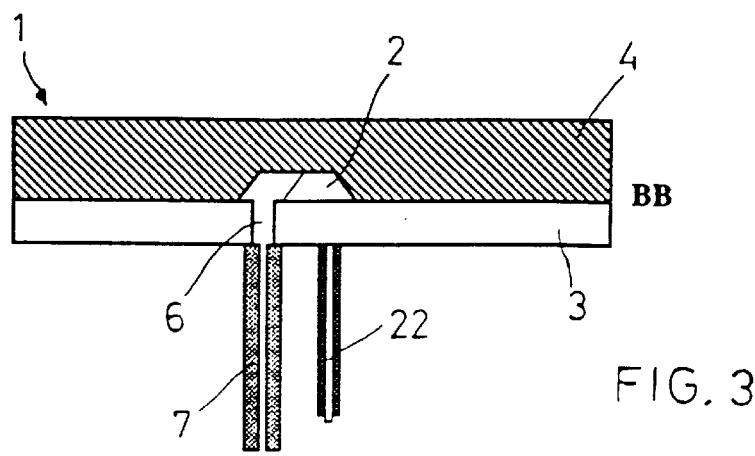
FIG. 3 is a schematic cross-sectional view along of the flow cell in FIG. 2 along line B—B as indicated on the sensor chip in FIG. 1.

FIG. 3 is a schematic cross-sectional view of the flow cell 1 according to the invention along line B—B as indicated on the sensor chip 3 in FIG. 1.

With reference to FIG. 3, fluid is introduced into the flow channel 2 through an inlet opening 6 in the sensor chip 3 by means of an inlet capillary tube 7 or other means. An outlet opening 8 for the fluid is indicated on the sensor chip 3 in FIG. 1, which outlet opening 8 is connected to an outlet capillary tube (not shown).

The inlet tube 7 and the outlet tube (not shown) for the fluid may be located in a fixture (not shown) on which the flow cell 1 is docked upon measurement, in which case the inlet opening 6 and the outlet opening 8 in the sensor chip 3 constitute the fluid interface of the flow cell 1.

The measurement area 5 of the sensor chip 3 is provided with sensor elements 9–13 for measuring different parameters of the fluid in the flow channel 2.

The sensor elements 9–13 which may be produced by thin film technique, are all electrically connected to contact pads 14, 15, 16, 17 and 18, respectively, on the sensor chip 3, which contact pads 14–18 in their turn are connected, in a manner not shown, by gold wires to connecting pins forming the electrical interface to the flow cell 1.

In the embodiment of the sensor chip 3 shown in FIG. 1, the sensor element 9 measures pH, and may comprise a known pH sensor in the form of an ion sensitive field effect transistor (ISFET) or a light-addressable potentiometric sensor (LAPS).

The sensor element 10 is adapted to measure the flow rate of the fluid in the flow channel 2, and may comprise in a manner not shown a known thermocouple and a known heating resistor.

The sensor elements 11 are adapted to measure the conductivity of the fluid. According to an alternative embodiment, one of the sensor elements 11 may be located in the silicon wafer 4 above the sensor element 11 located on the sensor chip 3.

The sensor element 12 is in the embodiment shown in FIG. 1, adapted to measure the pressure of the fluid, while sensor element 13 is adapted, in a manner known per se, to measure the temperature of the fluid.

According to the invention, the flow cell 1 is adapted to measure light absorption of the fluid in the flow cell as well as fluorescence and turbidity of the fluid in the flow cell.

To accomplish this in the embodiment shown on the drawing, an optical fibre 19 (FIG. 2) is provided to transmit light into the flow channel 2 through the transparent sensor chip 3. It should be pointed out that "fibre 19" actually can comprise more than one fibre. Also, it is to be understood that the fibre 19 may be replaced by a light source, e.g. a laser diode.

To measure light absorption of the fluid in the flow cell, UV, IR or visible light is transmitted into the flow cell through the optical fibre 19. The light transmitted into the flow cell is reflected by the inclined end wall 20 of the flow channel 2 towards the other end wall 21 of the flow channel 2, which end wall 21 is also inclined to reflect the light towards an optical fibre 22 which in a manner not shown is connected to a device (not shown) for measuring light absorption of the fluid. Also "fibre 22" may comprise more than one fibre. The fibre 22 can be replaced by a light receiver, e.g. a photodiode. It is actually to be understood that combinations of optical fibres, laser diodes, and photodetectors may used in any desired combination and manner.

To measure the fluorescence of the fluid, excitation light from e.g. a laser (not shown) may be conducted into the flow channel 2 through the optical fibre 19, and fluorescence may be picked up by an optical fibre 23 and conducted to a fluorescence detector (no shown).

As an alternative to a single fibre 23 located between the fibres 19 and 22, a bundle of fibres can be provided. One fibre may then be adapted to transmit excitation light into the fluid while the other fibres are adapted to receive the fluorescence from the fluid. Also in this case, the optical fibres may be replaced by a laser diode and a photodetector.

To measure the turbidity of the fluid in the flow cell, light, UV, IR or visible, is transmitted into the flow channel 2 by means of the optical fibre 19 and received by the optical fibre 23 which is then connected to a device for measuring the turbidity.

In the embodiment shown, the transparent sensor chip 3 constitutes the optical interface to the flow cell 1. The optical fibres 19, 22 and 23 may also be fixed in the above-mentioned fixture (not shown) on which the flow cell 1 is docked upon measurement together with the inlet and outlet capillary tubes for the fluid.

In that case, an integrated fluid and optical interface would be obtained. To secure the optical fibres and the capillary tubes in the fixture, the latter could be provided with V-grooves, and the optical fibres and the capillary tubes could be embedded by a polymer material in the V-grooves.

In case the optical fibres are replaced by combinations of laser diodes and photodetectors, the latter components may also be fixed in said fixture.

It is also possible to make the sensor chip 3 of a non-transparent material. In that case, the sensor chip 3 has to be provided with openings or transparent windows (not shown) for the optical fibres 19, 22 and 23. Those openings or transparent windows would then constitute the optical interface of the flow cell.

According to one embodiment of the invention and as apparent from FIGS. 2 and 3, both the cross-section of the flow channel 2 and the longitudinal section of the flow channel 2 has the form of a truncated, equally sided triangle.

When the flow channel, according to the described embodiment of the invention, is anisotropically etched in silicon, as apparent from the embodiment shown in FIG. 2, the optical fibres 19 and 22 have to be slightly inclined in order for the light transmitted into the flow cell through the fibre 19 to be reflected straight through the flow cell by the end wall 20 thereof and for the light reflected by the end wall 21 to be received by the optical fibre 22.

To increase the light transmission of the flow cell according to the invention, the surfaces of the flow channel may be coated with a layer of a reflective material, e.g. a thin aluminium film which may be deposited by means of sputtering or PVD.

If the chemical resistance of the reflective layer is poor, as is the case with an aluminium layer, this can be remedied by depositing a further layer, e.g. of $SiO_2$, on the aluminium layer.

It should also be pointed out that instead of producing a flow channel by etching, a flow channel can be defined between two flat surfaces which are kept separated by means of intermediate spacers.

As apparent from the above description, the flow cell according to the invention constitutes a multisensor for measuring any parameter associated with liquid chromatography measurements in one and the same very small volume of the fluid.

However, it is to be understood that the use of the flow cell according to the invention is not limited to the field of liquid chromatography, but it can equally well be used in connection with capillary electrophoresis, flow injection analysis (FIA) for general biotechnical processes or applications of similar nature, chemical/biochemical reactors etc.

We claim:

1. An apparatus for continuously measuring at least six total physical and chemical parameters in a fluid flow, characterized in that said apparatus comprises a single flow cell having a fluid interface for conducting the fluid through the flow cell, and elements for measuring at least six physical and/or chemical parameters, wherein said elements comprise an electrical interface connected to at least one first means provided in the flow cell wall for measuring at least one first parameter of the fluid in the flow cell, and an optical interface for transmitting light into the flow cell and for receiving light from the flow cell to measure at least one second parameter of the fluid in the flow cell.

* * * * *